United States Patent
Goren et al.

(10) Patent No.: US 8,758,993 B2
(45) Date of Patent: Jun. 24, 2014

(54) SYSTEMS AND METHODS FOR PREDICTING RESPONSE TO ANTI-ANDROGEN THERAPY FOR THE TREATMENT OF ANDROGENETIC ALOPECIA

(71) Applicant: Global Life Science Partners Limited, Central (HK)

(72) Inventors: Andy Ofer Goren, Newport Beach, CA (US); John McCoy, Downey, CA (US)

(73) Assignee: Global Life Science Partners Limited, Central (HK)

( * ) Notice: Subject to any disclaimer, the term of this patent is extended or adjusted under 35 U.S.C. 154(b) by 0 days.

(21) Appl. No.: 13/652,463

(22) Filed: Oct. 15, 2012

(65) Prior Publication Data

US 2013/0095484 A1    Apr. 18, 2013

Related U.S. Application Data

(60) Provisional application No. 61/547,654, filed on Oct. 14, 2011.

(51) Int. Cl.
*C12Q 1/00* (2006.01)
*G01N 33/53* (2006.01)

(52) U.S. Cl.
USPC ............................. 435/4; 435/7.1; 435/7.72

(58) Field of Classification Search
None
See application file for complete search history.

(56) References Cited

PUBLICATIONS

Randall et al. 1992. J. Invest Dermatol. 98:86S-91S.*
Giulani et al. 2010. J. Invest Dermatol. 130 Suppl 1, p. S102, #607.*
Brozic et al. 2011. Current Med. Chem 18:2554-2565.*
Halim et al. 2008. JACS 130:14123-14128.*
Eicheler et al. 1998. Arch. Dermatol. Res. 290:126-132.*
Rodriguez et al. 2010. ACS Chemical Biol. 5:1045-1052.*
PCT International Search Report and Written Opinion, Date of Mailing: Mar. 29, 2013, International Application No. PCT/US2012/060321, International Filing Date: Oct. 15, 2012, Authorized Officer:Sung Hee Choi.

* cited by examiner

*Primary Examiner* — Shulamith H Shafer
(74) *Attorney, Agent, or Firm* — Nixon Peabody LLP; Khaled Shami

(57) ABSTRACT

Methods, processes, systems, and apparatuses are disclosed for predicting anti-androgen therapy response in the treatment of androgenetic alopecia based on a fluorometric assay and proteomics.

4 Claims, 2 Drawing Sheets

SYSTEMS AND METHODS FOR PREDICTING RESPONSE TO ANTI-ANDROGEN THERAPY FOR THE TREATMENT OF ANDROGENETIC ALOPECIA

CROSS-REFERENCE TO RELATED APPLICATIONS

This application claims priority to U.S. Provisional Application No. 61/547,654, filed Oct. 14, 2011, entitled "System and Method for a Proteomics-Based Screen for Early Onset Androgenetic Alopecia and Anti-Androgen Therapy Response," which is incorporated herein by reference in its entirety.

TECHNICAL FIELD

The inventions described here relate to systems and methods for predicting anti-androgen response in the treatment of androgenetic alopecia.

BACKGROUND

Hair loss is associated with a variety of psychological and social implications. Prior to starting any treatment it is advantageous to predict the course, severity, and treatment options of the disease. In the field of hair loss, very little scientific diagnostic tests are currently available, and there are few methods to predict treatment response.

Moreover, the hair loss industry is littered with dozens of products that claim to grow, improve, and replace hair. Unfortunately, few treatments have been scientifically demonstrated to work, and the few treatments that have undergone clinical trials often do not work equally for all patients.

Androgenetic alopecia has been successfully treated in men by the U.S. Food & Drug Administration ("FDA") approved medication Finasteride (marketed as Propecia) as well as by off-label anti-androgen drugs. The drugs ultimately influence gene transcription mediated by the Androgen Receptor complex.

Among various individuals, whether male or female, there is a broad variability in the response of different people to various hair loss treatments. This variability is a result of a complex interaction of genetic and physiological factors contributing to variable androgen receptor control of gene transcription, making a one-size-fits-all approach difficult to achieve. It would therefore be advantageous to be able to have an effective diagnostic method where patients could be selected and treated on the basis of direct physiological activity assay, which would identify some people as being likely to benefit from treatment by anti-androgen therapies, while identifying other individuals in which treatment is not likely to be effective.

BRIEF SUMMARY

The inventions described here relate to systems and methods for predicting anti-androgen therapy response, such as in the treatment of androgenetic alopecia. Various embodiments are possible, a number of which are exemplified here.

In one embodiment of the present disclosure, a method is provided for predicting the likely response of a human subject to an anti-androgen therapy, comprising the steps of: obtaining a genetic sample from the subject; subcloning into a protein expression system at least a portion of an androgen receptor gene within said genetic sample, said portion containing a glutamine repeat sequence in exon 1 of said gene; expressing said portion, thereby producing a plurality of copies of a protein; purifying said protein; determining the number of glutamine repeats in said protein; comparing said number to one or more standardized values, each standardized value representing either high or low expected anti-androgen response for a class of patients including the subject, thereby producing an indication of either high or low expected anti-androgen response for the subject; and presenting the indication to the subject.

In another embodiment described herein a method is provided for predicting the likely response of a human subject to an anti-androgen therapeutic drug for the treatment of androgenic alopecia, comprising the steps of: obtaining a first hair follicle sample from the subject, the sample comprising at least one hair follicle; combining the first hair follicle sample with the anti-androgen therapeutic drug, a predetermined amount of testosterone, and a fluorogenic dye which competes with dihydrotestosterone (DHT) for reaction with aldo-ketoreductase 1C2 (AKR1C2), wherein the reaction of the fluorogenic dye with AKR1C2 results in a fluorescent product; incubating the first sample for a pre-determined time, at a temperature at which AKR1C2 is active; measuring a first fluorescence intensity of the first sample at a wavelength emitted by the fluorescent product; and comparing the first fluorescence intensity with a comparison value.

In yet another embodiment disclosed herein, a method is provided for predicting the likely response of a human subject to an anti-androgen therapeutic drug for the treatment of androgenic alopecia, comprising the steps of: obtaining a first hair follicle sample from the subject, the sample comprising at least one hair follicle; combining the first hair follicle sample with the anti-androgen therapeutic drug, a predetermined amount of testosterone, and a recombinant yeast strain comprising a plasmid that expresses human recombinant androgen receptor (hAR), said plasmid comprising an androgen response element (ARE) promoting the expression of a reporter gene, such that the reporter gene will be expressed when activated hAR binds to the ARE; incubating the first sample for a pre-determined time, at a temperature at which the recombinant yeast strain is active; measuring a value representing the degree of expression of the reporter gene; and comparing said value with a comparison value.

In another embodiment disclosed herein, a method is provided for predicting the likely response of a human subject to an anti-androgen therapeutic drug for the treatment of androgenic alopecia, comprising the steps of: obtaining a first hair follicle sample from the subject, the sample comprising at least one hair follicle; combining the first hair follicle sample with the anti-androgen therapeutic drug and a predetermined amount of testosterone; incubating the first sample for a pre-determined time, at a temperature at which cells within the hair follicle are active; conducting an ELISA or lateral flow assay to measure a first level of DHT or testosterone within the sample; and comparing said first level with a comparison value.

Various embodiments and variations of the inventions described herein are also provided, and various modification and variations will be suggested to one of skill in the art having the benefit of this disclosure.

BRIEF DESCRIPTION OF THE DRAWINGS

The accompanying drawings, which are incorporated into this specification, illustrate one or more exemplary embodiments of the inventions disclosed herein and, together with the detailed description, serve to explain the principles and exemplary implementations of these inventions. One of skill in the art will understand that the drawings are illustrative only, and that what is depicted therein may be adapted based on the text of the specification or the common knowledge within this field.

In the drawings, where like reference numerals refer to like reference in the specification.

DETAILED DESCRIPTION

The description herein is provided in the context of system and method for predicting anti-androgen therapy response in the treatment of androgenetic alopecia. Those of ordinary skill in the art will realize that the following detailed description is illustrative only and is not intended to be in any way limiting. Other embodiments will readily suggest themselves to such skilled persons having the benefit of this disclosure. Reference will now be made in detail to implementations as illustrated in the accompanying drawings. The same reference indicators will be used throughout the drawings and the following detailed description to refer to the same or like parts.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

The human proteome contains an enormous amount of information predictive of certain risks, benefits, and responses to certain diseases and treatments. Association studies of androgen receptor protein variations, such as the exon 1 glutamine repeat, may be associated with response to anti-androgen therapy in the treatment of androgenetic alopecia. A variation in an individual's androgen receptor protein may be compared to a reference database used herein to provide individuals with a computerized readout of their likelihood that they will respond to anti-androgen therapy.

Figure 1:
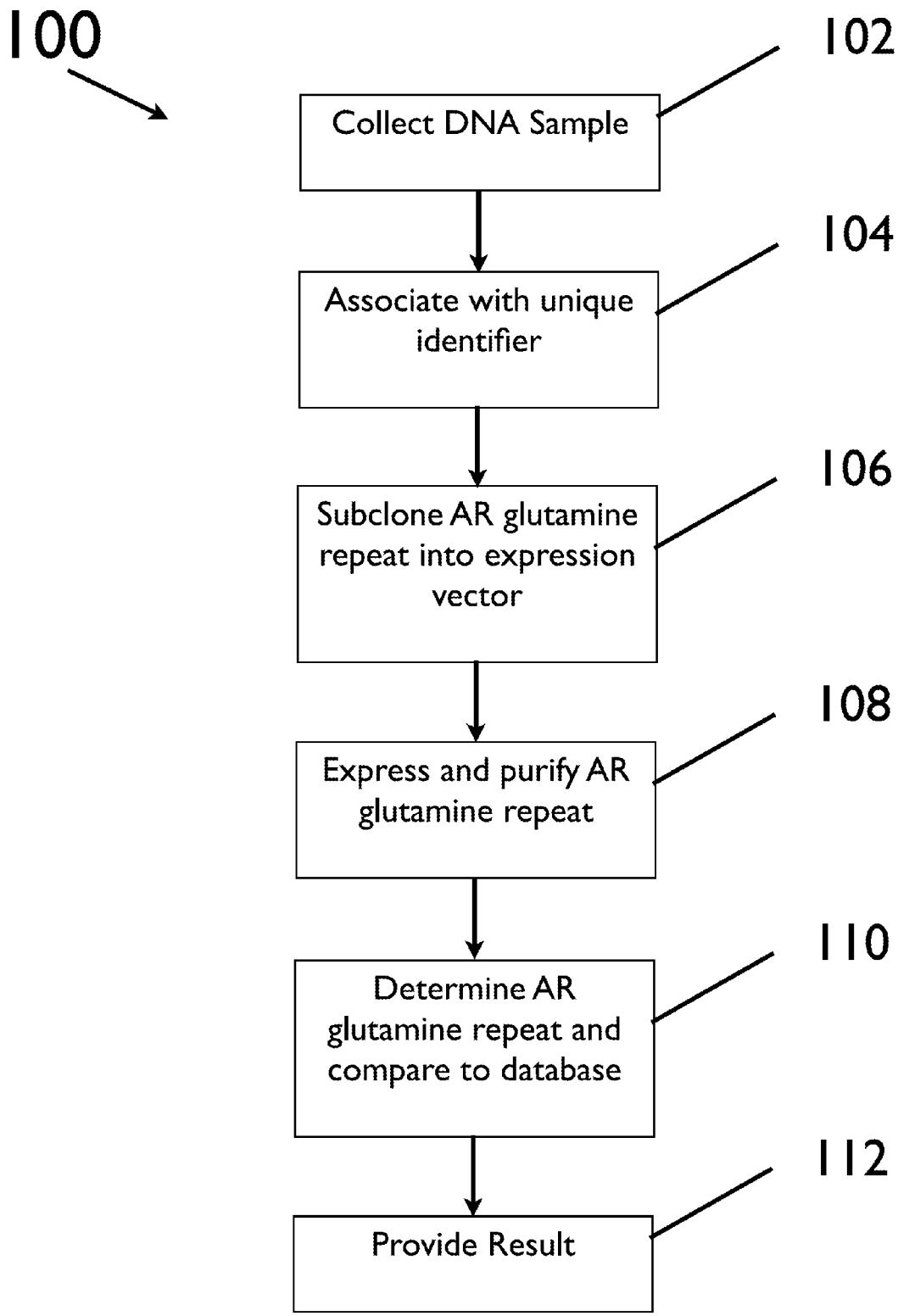
FIG. 1 is a flowchart showing a method of analyzing one or more DNA samples and providing a result.

With reference to FIG. 1, an example method 100 as described herein includes, at 102, collection of a DNA sample from a subject. Then, at 104, the DNA sample may be coded with a unique identifier, for instance to protect privacy and facilitate handling. At 106, a portion of the androgen receptor gene containing the glutamine repeat in the first exon of the androgen receptor gene in the DNA sample may be subcloned into a protein expression system. A variety of subcloning techniques can be used, including TOPO cloning, TA cloning, standard restriction enzyme digestion cloning, directional subcloning, etc. At 108, the subcloned glutamine repeat construct may be expressed and purified. The expression and protein purification can be accomplished by a number of techniques, including bacterial expression, eukaryotic expression, cell-free expression, His-tag pulldown on magnetic beads, cobalt or nickel-based affinity chromatography, alternative affinity chromatography, selective precipitation, a combination of one or more of the above techniques, etc. Then at 110, the number of glutamine repeats in the expressed proteins may be determined and compared to a database to determine a patient's likelihood to respond to anti-androgen therapies, such as finasteride, dutasteride, spironolactone, cyproterone acetate, flutamide, ketoconazole, and other similar compounds or compounds with anti-androgen activity for the treatment of androgenetic diseases, such as androgenetic alopecia, acne, hirsutism, polycystic ovarian syndrome, etc. The glutamine repeat length can be determined by a number of methods, including but not limited to polyacrylamide gel electrophoresis (PAGE), western blotting, mass spectrometry, high-performance liquid chromatography (HPLC) or a combination of one more of the methods. The database can take into account a patient's ethnicity and gender, and in another embodiment could also take into account a patient's family history of hair loss.

The results of the analysis may then be provided to the subject or to the caregiver of the subject at 112. The results of the analysis, each associated with its unique identifier, can be transmitted to a computer system that may include a Web-based server that is accessible, with proper authentication for instance using the unique identifier, by the subject or caregiver. The result may include a prediction of the likelihood to respond to anti-androgen therapies by comparing a patient's proteomic analysis to a reference database.

Figure 2:
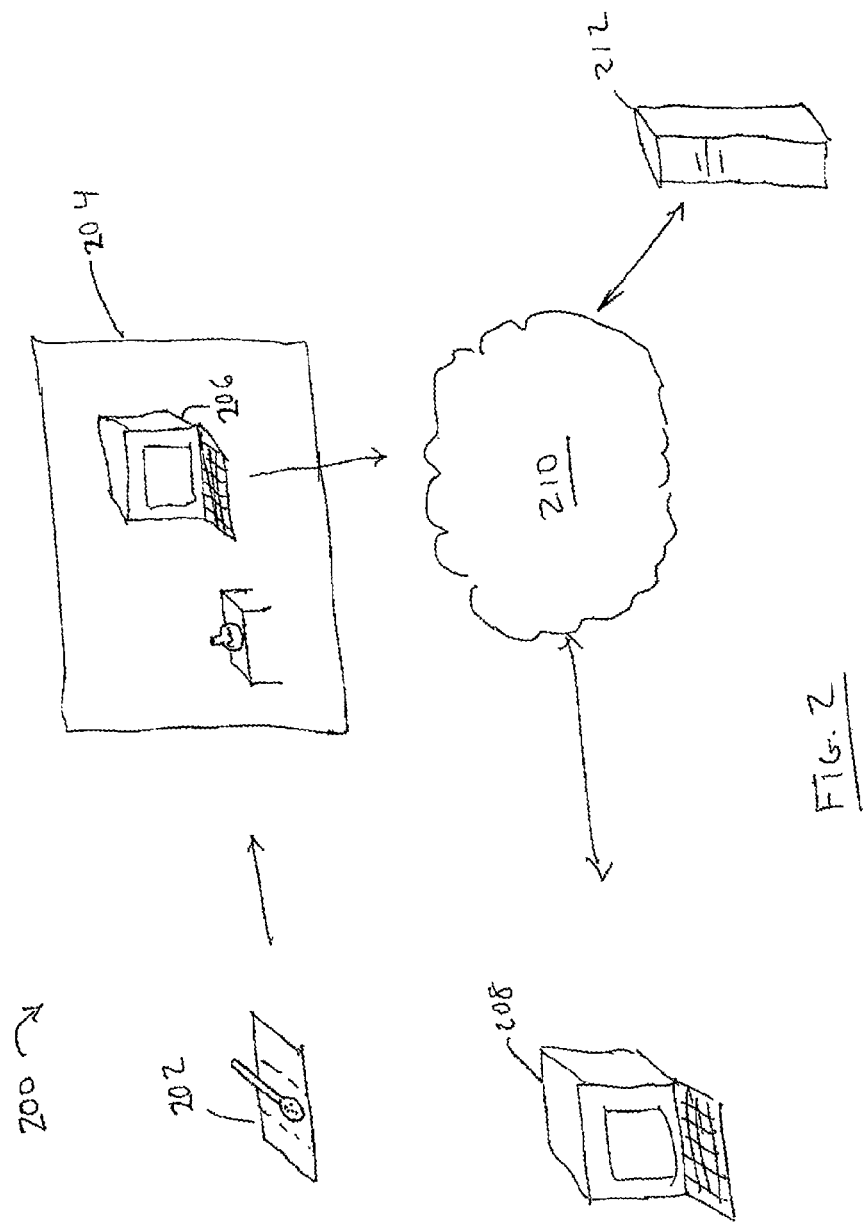
FIG. 2 shows an example of a computerized system for conducting or analyzing an assay to test DNA samples and providing a result.

FIG. 2 schematically shows a system 200 for implementing the above procedure. A sample 202 of DNA from a subject may be sent to a lab 204. An analysis of the sample in accordance with one or more of the aforementioned procedures may then be conducted. For example, results of the analysis may be compared with a database to generate an indication of the likelihood that a patient will respond to anti-androgen therapy for the treatment of their hair loss. The outcome of the comparison and analysis can be forwarded to the subject's or caregiver's computer system 208, for example electronically by way of a network, such as the Internet, 210. Alternatively or in addition, the outcome of the comparison and analysis can be stored on a server 212 for accessing remotely by the subject or caregiver following proper authentication that may require reference to the unique identifier to preserve privacy.

It may also be possible to use a neural network to implement the testing system and method, to predict the likelihood of a patient anti-androgen therapy response based on the patient's proteomic profile. According to such an approach, a method for predicting baldness may include: (a) constructing a N-layer neural network; (b) training the neural network with a data set of patients who have characteristics that relate to response to anti-androgen therapy for the treatment of hair loss; (c) obtaining a genetic sample from the subject; (d) generating a proteomics based profile from the sample, the profile being a function of values associated with a prescribed set of human protein variations; (e) obtaining a difference vector from the profile; (f) inputting the difference vector into the neural network.

The above are exemplary modes of carrying out the invention and are not intended to be limiting. It will be apparent to those of ordinary skill in the art that modifications thereto can be made without departure from the spirit and scope of the invention as set forth in the following claims. Various example embodiments of the present inventions are described herein in the context of a therapy for androgenetic alopecia.

In all the examples described herein, samples may include hair follicles, scalp tissue obtained from biopsy, or other relevant tissue which is the subject of the anti-androgen therapy.

Androgenetic alopecia is extremely common, affecting approximately 60% of men and over 50% of females by the age of 60. Currently, there are two FDA approved medications for the treatment of androgenetic alopecia, finasteride and minoxidil. However, finasteride therapies that are successful at hair re-growth and maintenance in males have failed to show significant improvement in females.

In accordance with one approach described herein, a patient's hair follicle sample may be obtained. Preferably, at least two hair follicles may be obtained, so that if only one is analyzed, there will be at least one backup if needed.

The patient's hair follicle sample may be subjected to a fluorogenic assay to determine the level of testosterone metabolism in the presence and absence of an anti-androgen therapy. A patient's hair follicle sample (from 1 to n hair follicles) may be placed in a reaction mixture containing approximately 20-200 nM testosterone and a flourogenic dye, coumberone. Coumberone is a competitive substrate with dihydrotestosterone (DHT) for aldo-ketoreductase 1C2 (AKR1C2). When reacted with AKR1C2, DHT is metabolized to $3\alpha,17\beta$-androstanediol ($3\alpha$-diol). When reacted with AKR1C2, coumberone is metabolized to coumberol, which has a fluorescent emission at 525 nm and can be readily detected with a monochrometer and an excitation light source (350 nm). As such, a solution containing a certain amounts of DHT will have a particular inhibitory effect on the conversion of coumberone to coumberol and can be detected. Blocking the conversion of testosterone to DHT is the mechanism of action of several anti-androgen therapies (e.g. finasteride). As such, incubating a patient's hair sample with testosterone either in the presence or absence of anti-androgen therapies can be compared with a coumberone fluorogenic assay to suggest efficacy. A requirement of the assay is the presence of AKR1C2. In the event a subject's hair does not contain a sufficient amount of the endogenous protein, supplemental enzyme can be added to the reaction mixture.

In one embodiment, two hair samples may be used. One hair sample may be incubated with an anti-androgen therapeutic drug, preferably 20-100 nM finasteride, while the other hair sample is incubated without the drug, all other factors that might influence the reaction being essentially the same, and the results may be compared. Alternatively the result of incubation with the therapeutic drug may be compared with the result of a standardized result obtained by averaging the results of many patients who were known to exhibit a strong therapeutic response to the anti-androgen therapeutic drug.

In yet another embodiment of the present invention, the patient's hair follicle sample may be subjected to a yeast androgen bioassay to determine the level of testosterone metabolism in the presence and absence of an anti-androgen therapy. A patient's hair follicle sample (from 1 to n hair follicles) may be placed in a reaction mixture containing approximately 20-200 nM testosterone with or without an anti-androgen therapy. A recombinant yeast strain will be constructed containing a plasmid (pRR-AR-5Z) that expresses human recombinant androgen receptor (hAR). Also contained in the plasmid is an androgen response element (ARE) promoting the expression of a reporter gene (e.g. green fluorescent protein, yEGFP, luciferase, etc.). The reporter gene will be expressed when activated hAR binds to the ARE. As such, levels of DHT can be detected in solutions of incubated hair follicles by adding said solutions to cultures of active yeast containing the plasmid pRR-AR-5Z. Expression of yEGFP can be measured using a fluorometer and quantified. These values can be used to compare solutions from testosterone incubated follicles in the presence and absence of anti-androgen treatments. Differences in measured values would imply a likely positive response for that subject to the examined anti-androgen treatment.

In another embodiment, the patient's hair follicle sample may be subjected to an enzyme-linked immunosorbent assay (ELISA) to determine the level of testosterone metabolism in the presence and absence of an anti-androgen therapy. A patient's hair follicle sample (from 1 to n hair follicles) may be placed in a reaction mixture containing approximately 20-200 nM testosterone with or without an anti-androgen therapy for an incubation time of 4-24 hours. After incubation, the level of testosterone to DHT conversion can be measured by an ELISA assay of DHT or testosterone.

Alternatively to ELISA, a lateral flow immunoassay may be used in the same manner.

In one embodiment, any of the above reactions may take place in a transparent container with a lid or other opening in which the hair follicle samples may be inserted. In one non-limiting example, the total amount of liquid in the assay container may be about 0.2 ml.

The reaction may be mixed and then incubated for approximately 4 to 16 hours at 37° C. depending on the number of hair follicles used in the assay. Mixing may be by any mixing means known in the art, including shaking the container. Where a shorter incubation time is required for a greater number of hair follicles. In one embodiment, an assay that uses one hair follicle may be incubated for approximately 16 hours. In another embodiment, an assay that uses two hair follicles may be incubated for approximately four hours.

What is claimed is:

1. A method for predicting the likely response of a human subject to an anti-androgen therapeutic drug for the treatment of androgenic alopecia, comprising the steps of:
    obtaining a hair follicle sample from the subject, the sample comprising at least one hair follicle;
    combining the hair follicle sample with the anti-androgen therapeutic drug, a predetermined amount of testosterone, aldo-ketoreductase 1C2 (AKR1C2), and a fluorogenic dye which competes with dihydrotestosterone (DHT) for reaction with AKR1C2, wherein the reaction of the fluorogenic dye with AKR1C2 results in a fluorescent product;
    incubating the hair follicle sample for a pre-determined time, at a temperature at which AKR1C2 is active;
    measuring a fluorescence intensity of the hair follicle sample at a wavelength emitted by the fluorescent product; and
    comparing the fluorescence intensity with a comparison value, wherein a fluorescence intensity greater than the comparison value indicates that the subject is likely to respond to the anti-androgen therapeutic drug.

2. The method of claim 1, wherein the fluorogenic dye is coumberone.

3. The method of claim 1, wherein the step of combining, the step of incubating, and the step of measuring is conducted in a transparent container.

4. The method of claim 1, wherein the comparison value is obtained by a method comprising the following steps:
    obtaining a second hair follicle sample from the subject, the sample comprising at least one hair follicle;
    combining the second hair follicle sample with the fluorogenic dye, AKR1C2, and the predetermined amount of testosterone, without addition of the anti-androgen therapeutic drug;
    incubating the second sample for a pre-determined time, at a temperature at which AKR1C2 is active;

measuring a second fluorescence intensity of the second sample at the wavelength emitted by the fluorescent product, the comparison value being the second fluorescence intensity.

* * * * *